United States Patent
Belmont et al.

(10) Patent No.: US 8,999,955 B2
(45) Date of Patent: Apr. 7, 2015

(54) TETRAHYDROCYCLOPENTA[C]ACRIDINE DERIVATIVES AS KINASE INHIBITORS AND BIOLOGICAL

(75) Inventors: Philippe Olivier Belmont, Lyons (FR); Laurent Meijer, Roscoff (FR); Philip Cohen, Dundee (GB); Amaury Patin, Villeurbanne (FR); Johann Bosson, Etrembières (FR); Peter Gregory Goekjian, Lyons (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 622 days.

(21) Appl. No.: 12/735,463

(22) PCT Filed: Jan. 19, 2009

(86) PCT No.: PCT/IB2009/050179
§ 371 (c)(1),
(2), (4) Date: Jul. 19, 2010

(87) PCT Pub. No.: WO2009/090623
PCT Pub. Date: Jul. 23, 2009

(65) Prior Publication Data
US 2010/0285124 A1 Nov. 11, 2010

(30) Foreign Application Priority Data
Jan. 18, 2008 (FR) ..................... 08 00275

(51) Int. Cl.
C07D 221/18 (2006.01)
C07F 7/10 (2006.01)
A61K 31/695 (2006.01)
A61K 31/473 (2006.01)
C07D 219/04 (2006.01)
C07D 215/14 (2006.01)
C07D 215/20 (2006.01)
C07D 219/06 (2006.01)
C07F 7/08 (2006.01)

(52) U.S. Cl.
CPC ............ C07D 219/04 (2013.01); C07D 215/14 (2013.01); C07D 215/20 (2013.01); C07D 219/06 (2013.01); C07F 7/0812 (2013.01)

(58) Field of Classification Search
None
See application file for complete search history.

(56) References Cited

PUBLICATIONS

Belmont, P. et al. A New Route to Acridines: Pauson-Kand Reaction on Quinoline-Bearing 1-En-7-ynes Leading to Novel Tetrahydrocyclopenta[c]acridine-2,5-diones. Tetrahedron. 2005, No. 14, p. 2401, scheme 5.*
"Guidance for Industry: Q3C—Tables and List." US DHHS, FDA, CDER, CBER, Nov. 2003. Revision 1.*
"Alzheimer's disease." CNN Health, Obtained Oct. 9, 2010, URL:http://www.cnn.com/2003/HEALTH/conditions/09/24/alzheimers.drug.ap/index.html.*
Antonio R. Damasio, Alzheimer's Disease and Related Dementias, Cecil Textbook of Medicine, 20th edition (1996), vol. 2, pp. 1992-1996.*
MedlinePlus, "Dementia," Obtained Sep. 30, 2012, <http://www.nlm.nih.gov/medlineplus/dementia.html>.*
MedlinePlus, "Parkinson's Disease," Obtained Sep. 30, 2012, <http://www.nlm.nih.gov/medlineplus/parkinsonsdisease.html>.*
International Search Report for PCT/IB2009/050179, mailed Jun. 5, 2009.
Patin, Amaury et al., "A New Route to Acridines: Pauson-Khand Reaction on Quinoline-Bearing 1-En-7-ynes Leading to Novel Tetrahydrocyclopenta[c]acridine-2,5-diones", Synthesis, No. 14, (2005), pp. 2400-2406.
Matthews et al, "Targeting Protein Kinases for Cancer Therapy", Kinases and Cancer, Chapter 1, pp. 32-33, 2010 (John Wiley & Sons, Inc. (Hobeken, NJ).
Oumata et al, "Roscovitine-Derived, Dual-Specificity Inhibitors of Cyclin-Dependent Kinases and Casein Kinases 1", Journal of Medicinal Chemistry, 2008, 51(17), 5229-5242.

* cited by examiner

Primary Examiner — Alicia L Otton
(74) Attorney, Agent, or Firm — Nixon & Vanderhye P.C.

(57) ABSTRACT

The invention relates to kinase inhibitors of the formula (I) in which —$R_1$ to $R_4$=H; ether or polyether, amino; $NO_2$; NH-carbamate; NH—CO—R, with R such as defined above; $N_3$ and derivatives thereof of the 1,2,3-triazole type; —$R_5$=OH; halogen; —OR with R such as defined above; OH-carbamate; OH-carbonate; $NH_2$, NH-carbamate; NH—CO—R, with R such as defined above; $N_3$ and derivatives thereof of the 1,2,3-triazole type; $N(R_9,R_{10})$; —$R_5'$=H or a C1-C12 alkyl, —$R_6$=H; R; (R or R')$_3$—Si, with R such as defined above; optionally substituted aryl, heteroaryl; halogen (iodine); alkynyl; —$R_7$ and $R_8$=H, $C_1$-$C_{12}$ alkyl; —$R_9$ and $R_{10}$=H, R (or R') such as defined above. These compounds can be used as kinase inhibitors in particular for treating cancer.

15 Claims, 2 Drawing Sheets

TETRAHYDROCYCLOPENTA[C]ACRIDINE DERIVATIVES AS KINASE INHIBITORS AND BIOLOGICAL

Figure 1:
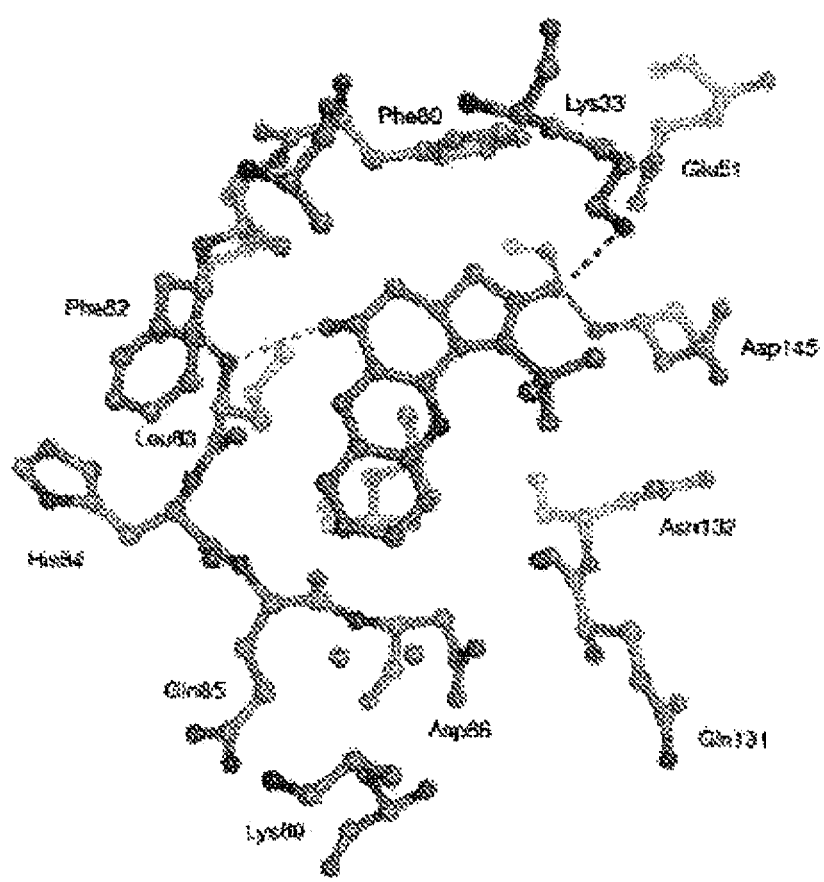

This application is the U.S. national phase of International Application No. PCT/IB2009/050179, filed 19 Jan. 2009, which designated the U.S. and claims the benefit of FR Application No. 08/00275, filed 18 Jan. 2008, the entire contents of each of which are hereby incorporated by reference.

The invention relates to tetrahydrocyclopenta[c]acridine derivatives as kinase inhibitors and is directed toward the use thereof as pharmacological tools and as medicaments.

It also relates to those of these derivatives which constitute new products.

The invention also relates to a process for the production thereof.

The inventors have a great deal of expertise regarding acridine derivatives which have led them to develop a particularly advantageous synthesis pathway, with a low number of stages starting, most generally, from commercially available products.

The development of their studies has resulted in a broadening of the family of these derivatives by synthesizing new tetrahydrocyclopenta[c]acridines.

The study of all these derivatives has made it possible to demonstrate, unexpectedly, inhibitory properties with respect to kinases which control cell division, for instance cyclin-dependent kinases (CDKs) and Aurora kinases, but also glycogen synthase kinase-3 (GSK-3).

By virtue of these inhibitory activities, these derivatives are particularly useful as active ingredients of medicaments for treating serious pathological conditions associated with dysregulation of these kinases.

The invention is therefore directed toward tetrahydrocyclopenta[c]acridine derivatives, as kinase inhibitors.

It also relates to these inhibitors for use as medicaments.

The invention also relates, as products, to those of these derivatives which are novel.

It is also directed toward a process for preparing these derivatives.

According to a first aspect, the invention is directed toward, as kinase inhibitors, tetrahydrocyclopenta[c]acridine derivatives corresponding to formula (I)

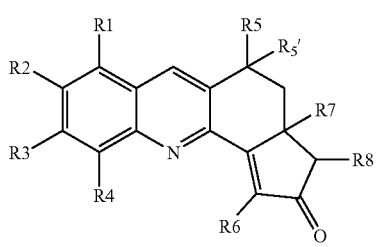

in which:
— $R_1$ to $R_4$, which may be identical or different, represent H; an ether or polyether radical —$(OR')_n$—OR, R and R', which may be identical or different, representing an optionally substituted, linear or branched $C_1$-$C_{12}$ alkyl radical; an amino group $NH_2$ or $N(R_9, R_{10})$; $NO_2$; NH-carbamate of —NH—CO-OM type, with M representing R (or R'), as defined above or a salt; NH—CO—R, with R as defined above; $N_3$ and derivatives thereof of 1,2,3-triazole type;

$R_5$ represents an —OH group; halogen; —OR with R as defined above; OH-carbamate of —O—CO—NHM type, with M representing R (or R'), as defined above; OH-carbonate of —O—CO-OM type, with M representing R (or R'), as defined above; $NH_2$, NH-carbamate of —NH—CO-OM type, with M representing R (or R'), as defined above or a salt; NH—CO—R, with R as defined above; $N_3$ and derivatives thereof of 1,2,3-triazole type; $N(R_9, R_{10})$, M and R being as defined above;

$R_5'$ represents H or a $C_1$-$C_{12}$ alkyl radical as defined above, or $R_5/R_5'$ together represents an =O group;

$R_6$ represents H; the R radical; an (R or R')$_3$—Si group, R being as defined above; an aryl radical, where appropriate substituted, a heteroaryl radical; a halogen (iodine); or an alkynyl radical —C≡C—R, with R as defined above;

$R_7$ and $R_8$, which may be identical or different, represent an H or a $C_1$-$C_{12}$ alkyl radical as defined above;

$R_9$ and $R_{10}$, which may be identical or different, represent H or the R (or R') radical as defined above, with the exception of the compounds in which $R_1$-$R_4$, $R_7$ and $R_8$=H; $R_5$ and $R_5'$ form a —C=O group, or $R_5$=OH and $R_5'$=H (or vice versa); $R_6$=—$(CH_3)_3$—Si, —$C_6H_5$, or $C_1$ or $C_4$ alkyl; and of the compound in which $R_1$-$R_4$, $R_7$ and $R_8$=H, $R_5$=—$OCH_3$ and $R_5'$=H (or vice versa), and $R_6$=$C_4$ alkyl.

In the description and the claims,

"alkyl" relates to a linear or branched, where appropriate substituted, hydrocarbon-based chain containing from 1 to 12 carbon atoms, preferably from 1 to 5 carbon atoms;

"halogen" represents F, Cl, Br, I and also the $CF_3$ group;

"aryl" represents one or more aromatic rings, where appropriate substituted, preferably a phenyl radical;

"heteroaryl" represents a heterocycle with N, O or S as heteroatom, which is, where appropriate, substituted, preferably a pyridyl or pyridinyl radical.

The invention is also directed toward the racemic forms of the above derivatives and also the enantiomeric forms thereof taken individually, more particularly the position-5, -7 and/or -8 isomers.

Advantageously, these derivatives are capable of blocking the ATP site of target kinases which are abnormally activated and therefore dysregulated, thus preventing their phosphorylation activity. Furthermore, these derivatives exhibit a selectivity with respect to these kinases in tests carried out on a panel of 70 kinases.

In this application as kinase inhibitors, the derivatives defined above make it possible to study the functions of the kinases in cell models and the effects resulting from the dysregulation of said kinases (overexpression or abnormal activation) in pathological conditions such as cancers, neurodegenerative diseases, diabetes, in particular type II diabetes, inflammatory diseases, depression and bipolar disorders or viral infections.

Derivatives which are preferred for use as kinase inhibitors correspond to inhibitors which are CDK-selective and which exhibit $IC_{50}$ values of less than 20 µM with respect to CDK1 and CDK5, in particular less than 10 µM, particularly advantageous derivatives having $IC_{50}$ values of less than 2 µM.

Derivatives corresponding to these characteristics are chosen from the group comprising:

5-hydroxy-1-trimethylsilanyl-3,3a,4,5-tetrahydro-2H-cyclopenta[c]acridin-2-one, 5-hydroxy-8-methoxy-1-trimethylsilanyl-3,3a,4,5-tetrahydro-2H-cyclopenta[c]acridin-2-one, 5-hydroxy-8,9-dimethoxy-1-trimethylsilanyl-3,3a,4,5-tetrahydro-2H-cyclopenta[c]acridin-2-one, 5-hydroxy-9-methoxy-1-trimethylsilanyl-3,3a,4,5-tetrahydro-2H-cyclopenta[c]acridin-2-one,
5-hydroxy-1-tert-butyl-3,3a,4,5-tetrahydro-2H-cyclopenta[c]acridin-2-one,
5-hydroxy-8-methoxy-1-tert-butyl-3,3a,4,5-tetrahydro-2H-cyclopenta[c]acridin-2-one,
5-hydroxyl-1-trimethylsilanyl-3-methyl-3,3a,4,5-tetrahydro-2H-cyclopenta[c]acridin-2-one,
5-hydroxy-9-methoxy-1-trimethylsilanyl-3-methyl 3,3a,4,5-tetrahydro-2H-cyclopenta[c]acridin-2-one,
5-chloro-1-trimethylsilanyl-3,3a,4,5-tetrahydro-2H-cyclopenta[c]acridin-2-one,
5-keto-3,3a,4,5-tetrahydro-2H-cyclopenta[c]acridin-2-one,
5-hydroxy-1-butanyl-3,3a,4,5-tetrahydro-2H-cyclopenta[c]acridin-2-one,
5-keto-1-trimethylsilanyl-3,3a,4,5-tetrahydro-2H-cyclopenta[c]acridin-2-one,
5-hydroxy-3,3a,4,5-tetrahydro-2H-cyclopenta[c]acridin-2-one.

5-Hydroxyl-trimethylsilanyl-3,3a,4,5-tetrahydro-2H-cyclopenta[c]acridin-2-one constitutes a particularly preferred kinase inhibitor, with $IC_{50}$ values of 0.56 to 0.74 μM with respect to CDK1 and 1.6 to 2.3 μM with respect to CDK5. This derivative was co-crystallized in the ATP site of CDK2-cyclin A (see FIG. 1). This co-crystal constitutes a new product and, in this respect, is part of the field of the invention. The representation given in FIG. 1 was performed with the group at R6 of tert-butyl type in place of the trimethylsilanyl group actually present, given that the silicon atom (Si) is not available in the processing software used.

Derivatives of this group which are also advantageous exhibit an $IC_{50}$ with respect to GSK-3 of less than 10 μM.

The inhibitory activity of the derivatives defined above confers on them a great advantage for treating pathological conditions related to kinase dysregulation.

According to a second aspect, the invention is therefore directed toward the derivatives of formula (I) above, for use as medicaments, including those in which $R_1$-$R_4$, $R_7$ and $R_8$=H; $R_5$ and $R_5'$ form a —C=O group, or $R_5$=OH and $R_5'$=H (or vice versa); $R_6$=—($CH_3$)$_3$—Si, —$C_6H_5$, or a $C_1$ or $C_4$ alkyl; and the compound in which $R_1$-$R_4$, $R_7$ and $R_8$=H, $R_5$=—$OCH_3$ and $R_5'$=H (or vice versa), and $R_6$=$C_4$ alkyl.

The invention is thus more particularly directed toward pharmaceutical compositions characterized in that they contain a therapeutically effective amount of at least one tetrahydrocyclopenta[c]acridine derivative as defined above, and also the compounds in which $R_1$-$R_4$, $R_7$ and $R_8$=H; $R_5$ and $R_5'$ form a —C=O group, or $R_5$=OH and $R_5'$=H (or vice versa); $R_6$=—($CH_3$)$_3$—Si, —$C_6H_5$, or $C_1$ or $C_4$ alkyl; and of the compound in which $R_1$-$R_4$, $R_7$ and $R_8$=H, $R_5$=—$OCH_3$ and $R_5'$=H (or vice versa), and $R_6$=$C_4$ alkyl, in combination with a pharmaceutically acceptable carrier.

These pharmaceutical compositions are advantageously in a form suitable for a given treatment according to the state of the patient and the pathological condition to be treated. Mention will more particularly be made of galenic forms for oral, parenteral or injectable administration.

In order to prepare these galenic forms, the active ingredients, used in therapeutically effective amounts, are mixed with the carriers that are pharmaceutically acceptable for the chosen method of administration.

For oral administration, the pharmaceutical compositions are more particularly in the form of tablets, gel capsules, capsules, pills, sugar-coated tablets, drops and the like.

Such compositions can contain from 1 to 100 mg of active ingredient per unit to be taken, in particular from 40 to 60 mg.

For intravenous, subcutaneous or intramuscular administration by injection, the pharmaceutical compositions are advantageously in the form of sterile or sterilizable solutions.

They contain from 10 to 50 mg of active ingredient, in particular from 20 to 30 mg.

These compositions are particularly effective for blocking the ATP site of CDKs and can thus in particular stop the anarchic cell division of cancer cells.

In addition to the treatment of cancers, these pharmaceutical compositions are also effective for treating neurodegenerative diseases, diabetes, in particular type II diabetes, inflammatory diseases, depression and bipolar disorders.

According to a third aspect, the invention is directed toward the derivatives of formula (I) above corresponding to new products. They are derivatives in which $R_1$ to $R_9$ are as defined above, with the exception of 5-hydroxy-1-trimethylsilanyl-3,3a,4,5-tetrahydro-2H-cyclopenta[c]acridin-2-one, 5-hydroxy-1-butanyl-3,3a,4,5-tetrahydro-2H-cyclopenta[c]acridin-2-one and 5-keto-1-trimethylsilanyl-3,3a,4,5-tetrahydro-2H-cyclopenta[c]acridin-2-one.

Preferred derivatives comprise:
5-hydroxy-8-methoxy-1-trimethylsilanyl-3,3a,4,5-tetrahydro-2H-cyclopenta[c]acridin-2-one,
5-hydroxy-8,9-dimethoxy-1-trimethylsilanyl-3,3a,4,5-tetrahydro-2H-cyclopenta[c]acridin-2-one,
5-hydroxy-9-methoxy-1-trimethylsilanyl-3,3a,4,5-tetrahydro-2H-cyclopenta[c]acridin-2-one,
5-hydroxy-1-tert-butyl-3,3a,4,5-tetrahydro-2H-cyclopenta[c]acridin-2-one,
5-hydroxy-8-methoxy-1-tertbutyl-3,3a,4,5-tetrahydro-2H-cyclopenta[c]acridin-2-one,
5-hydroxy-1-trimethylsilanyl-3-methyl-3,3a,4,5-tetrahydro-2H-cyclopenta[c]acridin-2-one,
5-hydroxy-9-methoxy-1-trimethylsilanyl-3-methyl-3,3a,4,5-tetrahydro-2H-cyclopenta[c]acridin-2-one,
5-chloro-1-trimethylsilanyl-3,3a,4,5-tetrahydro-2H-cyclopenta[c]acridin-2-one,
5-hydroxy-3,3a,4,5-tetrahydro-2H-cyclopenta[c]acridin-2-one.

Figure 2:
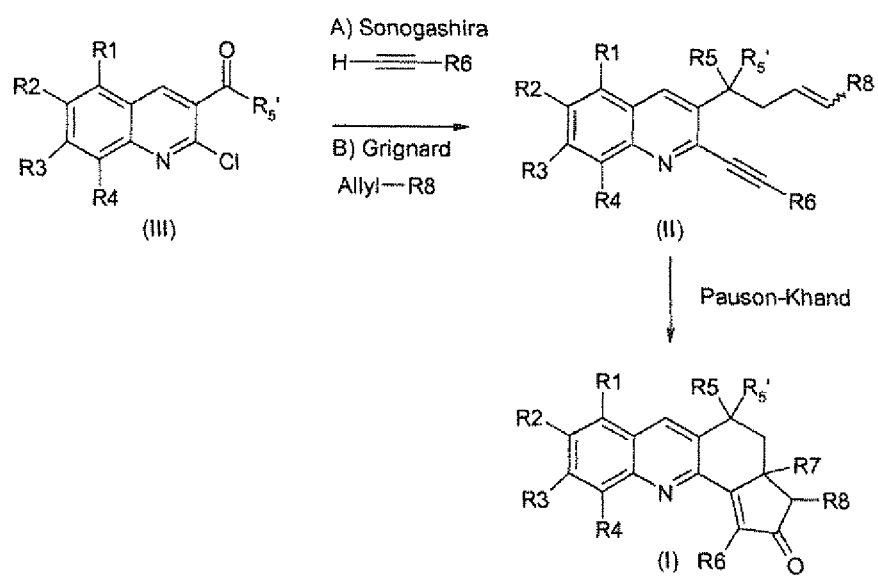

The derivatives of the invention are advantageously obtained according to the methodology described by Patin and Belmont (1) and illustrated by the scheme given in FIG. 2.

The principle of this process is also applied for obtaining the novel derivatives of the invention.

According to a fourth aspect, the invention is thus directed toward a synthesis process comprising:
the reaction of a derivative of formula (II)

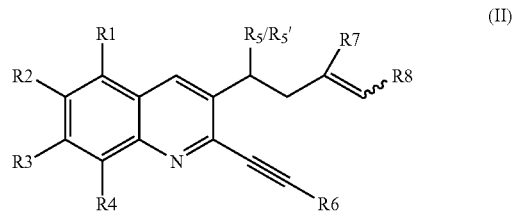

in which:
R1 to R7 are as defined above, and R8, defined as above, can be derivatized by means of a cross-metathesis reaction from the allyl or R8 represents H, in the presence of a catalyst such as $Co_2(CO)_8$ (or a rhodium or molybdenum complex), according to the Pauson-Khand reaction (1) (abbreviated to PKR), under conditions which make it possible to give a derivative of formula (I)

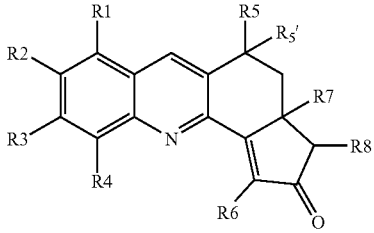

The derivatives in which R5 represents an OM group can be subjected to an oxidation step so as to obtain a derivative of formula (I) in which R5/R5' represent a ketone function.

The derivatives in which one of the substituents R1 to R5 represents an $N_3$ derivative of 1,2,3-triazole type are advantageously obtained by means of 1,3-dipolar reactions of "click chemistry" type (3).

The compound of formula (II) is advantageously obtained by means of a Sonogashira or Negishi reaction, using a 2-chloro-3-quinolinecarboxaldehyde derivative (R5' represents H or a $C_1$-$C_{12}$ alkyl radical as defined above) of formula (III)

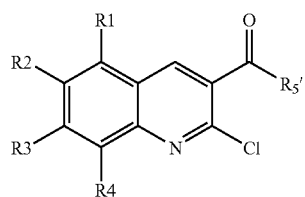

with an alkyne of formula (IV) $R_6$—C≡CH, followed by a Grignard reaction with the addition of allylmagnesium bromide or of another Grignard reagent substituted on the allyl function (R8).

The derivative (III) is itself preferably obtained from a derivative of formula (V)

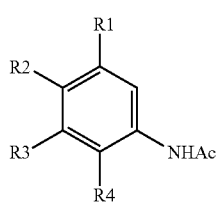

where Ac=$CH_3CO$—, by carrying out the process in an organic solvent such as DMF in the presence of $POCl_3$ under the conditions described by Meth-Cohn et al. (2).

The synthesis intermediate quinolinecarbaldehyde derivatives of formula (II) are new products and are therefore, as such, also covered by the invention.

Intermediate derivatives comprise 2-(trimethylsilanylethynyl)quinoline-3-carbaldehyde, 6-methoxy-2-(trimethylsilanylethynyl)quinoline-3-carbaldehyde, 6,7-dimethoxy-2-(trimethylsilanylethynyl) quinoline-3-carbaldehyde, and 7-methoxy-2-(trimethylsilanylethynyl)quinaline-3-carbaldehyde. Preferably, they are 1-(2-(trimethylsilanylethynyl) quinolin-3-yl)but-3-en-1-ol, 1-(6-methoxy-2-(trimethylsilanylethynyl)quinolin-3-yl)but-3-en-1-ol, 1-(6,7-dimethoxy-2-(trimethylsilanylethynyl) quinolin-3-yl)but-3-en-1-ol and 1-(7-methoxy-2-(trimethylsilanylethynyl) quinolin-3-yl)but-3-en-1-ol.

Other characteristics and advantages of the invention are given in the examples which follow.

FIGS. 1 and 2 represent, respectively, the structure of the co-crystal of 5-hydroxy-1-trimethylsilanyl-3,3a,4,5-tetrahydro-2H-cyclopenta[c]acridin-2-one with the ATP site of CDK2-cyclin A, and a scheme for the synthesis of tetrahydrocyclopenta[c]acridine derivatives.

EXAMPLE 1

Synthesis of Tetrahydrocyclopenta[c]Acridine Derivatives According to the Invention Sonogashira Reaction:

The halogenated quinoline-type derivative of formula (III) (1.00 mmol), $PdCl_2$ $(PPh_3)_2$ (35 mg, 0.05 mmol) and CuI (9 mg, 0.05 mmol) are mixed under an argon atmosphere. Once the system has been degassed, DMF (1 ml) and TEA (0.6 ml) are added to the reaction medium. The alkyne (1.10 mmol) is then added dropwise. The reaction medium is stirred at ambient temperature for 12 hours. The reaction medium is then filtered through silica and then evaporated. The residue obtained is purified by flash chromatography.

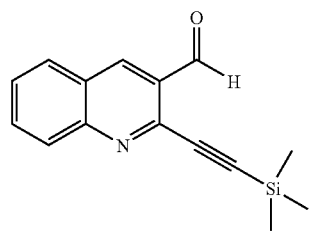 [SMILES: C[Si](C)(C)C#Cc1nc2ccccc2cc1C=O]

2-(Trimethylsilanylethynyl)quinoline-3-carbaldehyde

Mp 125° C.

IR: 2954, 2850, 2359, 2338, 1694, 1579, 1369, 1149, 1096 $cm^{-1}$.

$^1H$ NMR (300 MHz, $CDCl_3$): δ=10.70 (s, 1H), 8.72 (s, 1H), 8.16 (dd, 1H, J=8.5, 1.0 Hz), 7.95 (dd, 1H, J=8.1, 1.4 Hz), 7.85 (ddd, 1H, J=8.5, 7.0, 1.4 Hz), 7.63 (ddd, 1H, J=8.1, 7.0, 1.0 Hz), 0.34 (s, 9H);

$^{13}C$ NMR (75 MHz, $CDCl_3$): δ=191.0 (CH), 150.0 (C), 143.6 (C), 136.8 (CH), 133.0 (CH), 129.7 (CH), 129.4 (CH), 128.8 (C), 128.4 (CH), 126.5 (C), 102.5 (C), 100.1 (C), −0.3 ($CH_3$);

MS: m/z (%)=286 (81) [$MNa^+$], 254 (100) [$MH^+$], 180 (17) [$MH^+$-TMS].

MS-HR: m/z [$MH^+$] calculated for $C_{15}H_{15}NOSi$: 254.1001; found: 254.0997.

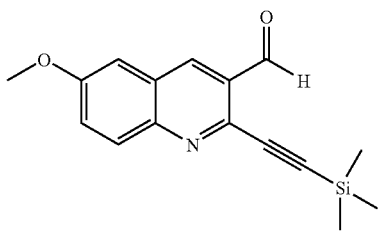

6-Methoxy-2-(trimethylsilanylethynyl)quinoline-3-carbaldehyde

Mp 155-156° C.

IR: 3051, 3001, 2964, 2840, 2158, 1694, 1243, 1226, 837 cm$^{-1}$.

$^1$H NMR (300 MHz, CDCl$_3$): δ=10.69 (s, 1H), 8.59 (s, 1H), 8.05 (d, 1H, J=9.3 Hz), 7.49 (dd, 1H, J=9.3, 2.8 Hz), 7.16 (d, 1H, J=2.8 Hz), 3.96 (s, 3H), 0.33 (s, 9H);

$^{13}$C NMR (75 MHz, CDCl$_3$): δ=191.3 (CH), 159.1 (C), 146.4 (C), 141.2 (C), 135.0 (CH), 130.8 (CH), 129.1 (C), 127.9 (C), 126.3 (CH), 106.2 (CH), 101.4 (C), 100.2 (C), 55.8 (CH$_3$), −0.2 (CH$_3$);

MS: m/z (%)=284 (28) [MH$^+$], 316 (100) [M+CH$_3$OH+H$^+$].

MSHR: m/z [MH$^+$] calculated for C$_{16}$H$_{17}$NO$_2$Si: 284.1107; found: 284.1112.

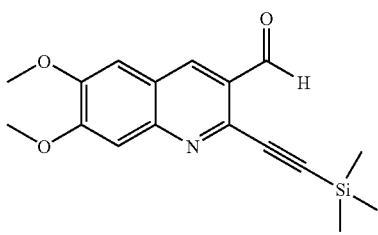

6,7-Dimethoxy-2-(trimethylsilanylethynyl)quinoline-3-carbaldehyde

Mp 188° C.

IR: 3015, 2957, 2931, 2860, 2830, 2163, 1688, 1257, 1215, 1113, 1008, 841 cm$^{-1}$.

$^1$H NMR (300 MHz, CDCl$_3$): δ=10.65 (s, 1H), 8.54 (s, 1H), 7.47 (s, 1H), 7.12 (s, 1H), 4.05 (s, 3H), 4.04 (s, 3H), 0.33 (s, 9H);

$^{13}$C NMR (75 MHz, CDCl$_3$): δ=191.2 (CH), 155.6 (C), 151.3 (C), 148.0 (C), 142.1 (C), 134.1 (CH), 127.9 (C), 122.8 (C), 107.9 (CH), 106.2 (CH), 101.4 (C), 100.4 (C), 56.6 (CH$_3$), 56.4 (CH$_3$), 0.2 (CH$_3$);

MS: m/z (%)=314 (100) [MH$^+$], 346 (85) [M+CH$_3$OH+H$^+$].

MSHR: m/z [MH$^+$] calculated for C$_{17}$H$_{19}$NO$_3$Si: 314.1212; found: 314.1207.

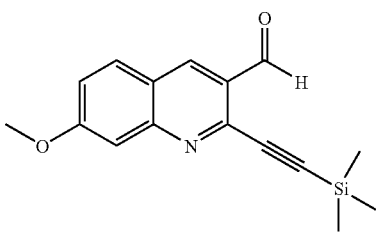

7-Methoxy-2-(trimethylsilanylethynyl)quinoline-3-carbaldehyde

Mp 142° C.

IR: 3008, 2959, 2896, 2856, 2830, 1687, 1495, 1210, 1131, 1016, 841 cm$^{-1}$.

$^1$H NMR (300 MHz, CDCl$_3$): δ=10.60 (s, 1H), 8.56 (s, 1H), 7.75 (d, 1H, J=9.0 Hz), 7.40 (d, 1H, J=2.3 Hz), 7.20 (dd, 1H, J=9., 2.3 Hz), 3.92 (s, 3H), 0.31 (s, 9H);

$^{13}$C NMR (75 MHz, CDCl$_3$): δ=190.8 (CH), 163.7 (C), 152.2 (C), 144.3 (C), 136.0 (CH), 130.8 (CH), 127.4 (C), 122.1 (C), 122.0 (CH), 107.2 (CH), 102.1 (C), 100.2 (C), 55.9 (CH$_3$), 0.2 (CH$_3$);

MS: m/z (%)=284 (58) [MH$^+$], 316 (100) [M+CH$_3$OH+H$^+$].

MSHR: m/z [MH$^+$] calculated for C$_{16}$H$_{17}$NO$_2$Si: 284.1107; found: 284.1111.

Grignard Reaction:

The derivative of 2-ethynylquinoline-3-carbaldehyde type (1.00 mmol) is dissolved in 10 ml of freshly distilled THF under an argon atmosphere. The reaction medium is cooled to 78° C. The commercially available 1M solution of allyl magnesium bromide in Et$_2$O (1.50 ml, 1.50 mmol) is then added dropwise. The reaction medium is stirred for 4 hours at −78° C. The reaction medium is then run into a saturated aqueous solution of NH$_4$Cl, the aqueous phase is extracted with ethyl acetate and the resulting organic phase is rinsed with a saturated aqueous solution of NaCl, dried over NaaSCa, filtered and evaporated. The residue obtained is purified by flash chromatography,

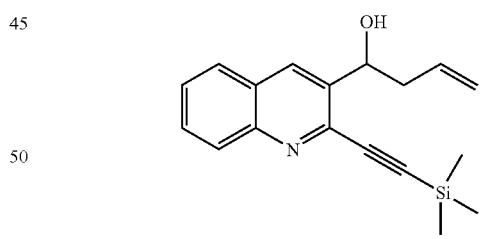

1-(2-(Trimethylsilanylethynyl)quinolin-3-yl)but-3-en-1-ol

Mp 111° C.

IR: 3232, 3074, 2958, 2899, 2161, 1247, 1060 cm$^{-1}$.

$^1$H NMR (300 MHz, CDCl$_3$): δ=8.29 (s, 1H), 8.09 (dd, 1H, J=8.4, 1.1 Hz), 7.79 (d, 1H, J=8.0, 1.4 Hz), 7.69 (ddd, 1H, J=8.5, 7.0, 1.4 Hz), 7.53 (ddd, 1H, J=8.0, 7.0, 1.1 Hz), 5.97-5.83 (m, 1H), 5.36-5.33 (m, 1H), 5.24 (dd, 1H, J=7.0, 1.1 Hz), 5.20 (s, 1H), 2.85 (m, 1H), 2.44 (m, 2H), 0.31 (s, 9H);

$^{13}$C NMR (75 MHz, CDCl$_3$): δ=147.3 (C), 141.2 (C), 138.8 (C), 134.4 (CH), 132.7 (CH), 129.9 (CH), 129.3 (CH), 129.2 (C), 127.8 (CH), 127.6 (CH), 119-1 (CH$_2$), 102.1 (C), 77.5 (C), 70.2 (CH), 42.9 (CH$_2$), 0.1 (CH$_3$);

MS: m/z (%)=296 (100) [MH$^+$].

MSHR: m/z [MH$^+$] calculated for C$_{18}$H$_{21}$NOSi: 296.1474; found: 296.1474.

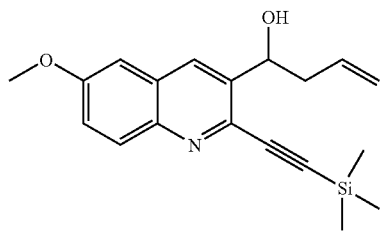 [SMILES: C=CCC(O)c1cc2cc(OC)ccc2nc1C#C[Si](C)(C)C]

1-(6-Methoxy-2-(trimethylsilanylethynyl)quinolin-3-yl)but-3-en-1-ol

Mp 149° C.

IR: 3252, 3075, 3012, 2961, 2937, 2901, 2830, 2161, 1621, 1492, 1239, 1027, 827 cm$^{-1}$.

$^1$H NMR (300 MHz, CDCl$_3$): δ=8.19 (s, 1H), 8.00 (d, 1H, J=8.8 Hz), 7.32 (dd, 1H, J=8.8, 2.7 Hz), 7.05 (d, 1H, J=2.7 Hz), 5.97-5.83 (m, 1H), 5.33-5.30 (m, 1H), 5.24 (d, 1H, J=6.4 Hz), 5.20 (s, 1H), 3.93 (s, 3H), 2.85 (m, 1H), 2.44 (m, 2H), 0.31 (s, 9H);

$^{13}$C NMR (75 MHz, CDCl$_3$): δ=147.3 (C), 141.2 (C), 138.8 (C), 134.5 (CH), 132.7 (CH), 129.9 (CH), 129.3 (CH), 129.2 (C), 127.8 (CH), 127.6 (CH), 119.2 (CH$_2$), 105.2 (CH), 102.1 (C), 77.5 (C), 70.3 (CH), 55.8 (CH$_3$), 43.0 (CH$_2$), 0.1 (CH$_3$);

MS: m/z (%)=326 (100) [MH$^+$].

MSHR m/z [MH$^+$] calculated for C$_{19}$H$_{23}$NO$_2$Si: 326.1576; found: 326.1571.

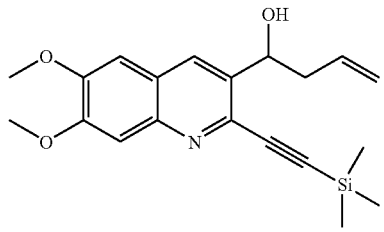 [SMILES: C=CCC(O)c1cc2cc(OC)c(OC)cc2nc1C#C[Si](C)(C)C]

1-(6,7-Dimethoxy-2-(trimethylsilanylethynyl)quinolin-3-yl)but-3-en-1-ol

Mp 65-67° C.

IR: 3367, 3077, 3003, 2959, 2929, 2851, 2159, 1621, 1497, 1244, 1213, 1008, 840 cm$^{-1}$.

$^1$H NMR (300 MHz, CDCl$_3$): δ=8.10 (s, 1H), 7.40 (s, 1H), 7.00 (s, 1H), 5.97-5.82 (m, 1H), 5.33-5.27 (m, 1H), 5.24 (dd, 1H, J=6.4, 1.5 Hz), 5.19 (s, 1H), 4.00 (s, 3H), 3.99 (s, 3H), 2.85-2.79 (m, 1H), 2.50-2.40 (m, 1H), 2.36 (s, 1H), 0.30 (s, 9H);

$^{13}$C NMR (75 MHz, CDCl$_3$): δ=152.4 (C), 150.2 (C), 143.8 (C), 138.1 (C), 137.6 (C), 134.6 (CH), 130.7 (CH), 123.2 (C), 117.9 (CH$_2$), 107.1 (CH), 104.6 (CH), 102.1 (C), 99.2 (C), 69.9 (CH), 55.9 (CH$_3$), 55.8 (CH$_3$), 42.7 (CH$_2$), −0.3 (CH$_3$);

MS: m/z (%)=356 (100) [MH$^+$].

MSHR m/z [MH$^+$] calculated for C$_{20}$H$_{25}$NO$_3$Si: 356.1682; found: 356.1677.

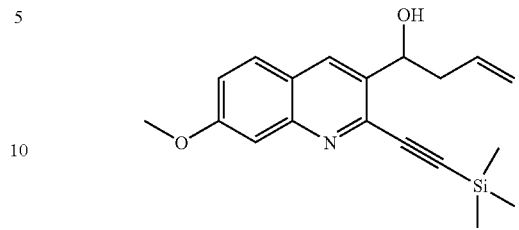

1-(7-Methoxy-2-(trimethylsilanylethynyl)quinolin-3-yl)but-3-en-1-ol

Mp 176-177° C.

IR: 3196, 3078, 3013, 2958, 2901, 2840, 2160, 1622, 1497, 1234, 1215, 1026, 839, 816 cm$^{-1}$.

$^1$H NMR (300 NHz, CDCl$_3$): δ=8.21 (s, 1H), 7.68 (d, 1H, J=9.0 Hz), 7.32 (d, 1H, J=2.5 Hz), 7.19 (dd, 1H, J=9.0, 2.5 Hz), 5.97-5.83 (m, 1H), 5.34-5.29 (m, 1H), 5.24 (d, 1H, J=6.0 Hz), 5.19 (s, 1H), 3.92 (s, 3H), 2.86-2.77 (m, 1H), 2.50-2.39 (m, 1H), 2.35 (d, 1H, J=3.6 Hz), 0.31 (s, 9H);

$^{13}$C NMR (75 MHz, CDCl$_3$): δ=161.0 (C), 149.0 (C), 141.1 (C), 136.7 (C), 134.4 (CH), 132.4 (CH), 128.7 (CH), 122.9 (C), 121.0 (CH), 119.0 (CH$_2$), 106.9 (CH), 102.2 (C), 100.3 (C), 70.2 (CH), 55.6 (CH$_3$), 43.0 (CH$_2$), −0.1 (CH$_3$);

MS: m/z (%)=326 (100) [MH$^+$].

MSHR m/z [MH$^+$] calculated for C$_{19}$H$_{23}$NO$_2$Si: 326.1576; found: 326.1582.

Pauson-Khand Reaction:

The quinoline enyne derivative of formula (II) (1.00 mmol) is dissolved in 10 ml of freshly distilled DCM under an argon atmosphere. Co$_2$(CO)$_8$ (420 mg, 1.20 mmol) is then added. The reaction medium is stirred for 2 hours at ambient temperature and the complexation of the metal on the alkyne is monitored by TLC. NMO (1171 mg, 10.00 mmol) is then added portionwise and the reaction medium is stirred for 12 hours at ambient temperature. The reaction medium is subsequently filtered through silica and then evaporated. The residue obtained is purified by flash chromatography.

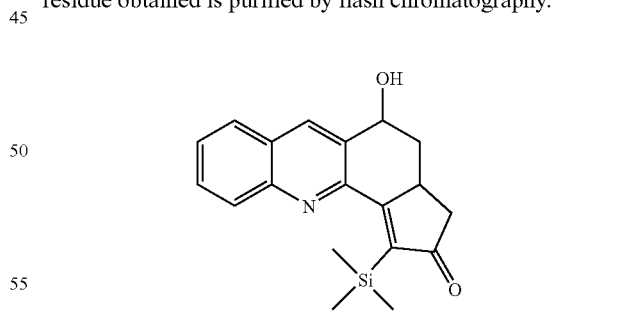

5-Hydroxy-1-trimethylsilanyl-3,3a,4,5-tetrahydro-2H-cyclopenta[c]acridin-2-one

Mp 167-168° C.

IR: 2968, 2950, 2894, 1686, 1273, 1157, 856 cm$^{-1}$.

$^1$H NMR (300 MHz, CDCl$_3$): δ=8.22 (s, 1H), 8.12 (dd, 1H, J=8.4, 0.9 Hz), 7.85 (dd, 1H, J=8.1, 0.9 Hz), 7.70 (ddd, 1H, J=8.4, 6.9, 0.9 Hz), 7.59 (ddd, 1H, J=8.1, 6.9, 0.9 Hz), 5.21-5.18 (m, 1H), 3.72-3.64 (m, 1H), 2.84 (dd, 1H, J=11.4, 6.6

Hz), 2.55-2.48 (m, 1H), 2.27 (dd, 1H, J=18.0, 3.9 Hz), 1.95 (ddd, 1H, J=13.5, 13.5, 3.3 Hz), 1.68 (m, 1H), 0.35 (s, 9H);

$^{13}$C NMR (75 MHz, CDCl$_3$): δ=212.1 (C), 179.3 (C), 149.9 (C), 147.6 (C), 142.7 (C), 137.4 (CH), 132.7 (C), 130.6 (CH), 129.5 (CH), 128.4 (C), 128.0 (CH), 127.8 (CH), 67.7 (CH), 43.7 (CH$_2$), 37.9 (CH$_2$), 35.4 (CH), 0.9 (CH$_3$);

MS: m/z (%)==324 (68) [MH$^+$], 306 (100) [MH$^+$—H$_2$O].

MSHR m/z [MH$^+$] calculated for C$_{19}$H$_{21}$NO$_2$Si: 324.1420; found: 324.1422.

Elemental analysis: found (calculated) C, 70.02 (70.55); H, 6.42 (6.54); N, 4.12 (4.33);

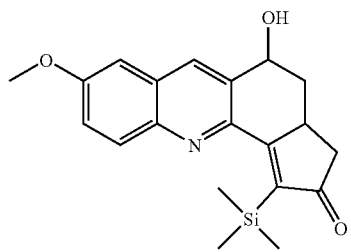 [SMILES: COc1ccc2nc3c(cc2c1)C(O)CC1CC(=O)C([Si](C)(C)C)=C31]

5-Hydroxy-8-methoxy-1-trimethylsilanyl-3,3a,4,5-tetrahydro-2H-cyclopenta[c]acridin-2-one Mp 186° C.

IR: 3357, 3001, 2955, 2888, 2825, 1659, 1490, 1216, 851; 840, 827 cm$^{-1}$.

NMR (300 MHz, CDCl$_3$): δ=8.05 (s, 1H), 7.95 (d, 1H, J=9.3 Hz), 7.35 (dd, 1H, J=9.3, 2.6 Hz), 7.01 (d, 1H, J=2.6 Hz), 5.10-5.06 (m, 1H), 3.88 (s, 3H), 3.69-3.60 (m, 1H), 2.72 (dd, 1H, J=17.8, 6.8 Hz), 2.47-2.42 (m, 1H), 2.17 (dd, 1H, J=17.9, 4.1 Hz), 1.85 (ddd, 1H, J=13.5, 13.5, 3.2 Hz), 1.25 (m, 1H), 0.35 (s, 9H);

$^{13}$C NMR (75 MHz, CDCl$_3$): δ=212.5 (C), 180.5 (C), 159.0 (C), 147.3 (C), 143.8 (C), 141.0 (C), 136.0 (CH), 133.3 (C), 130.8 (CH), 129.7 (C), 123.7 (CH), 104.9 (CH$_3$), 67.4 (CH), 55.7 (CH), 43.6 (CH$_2$), 37.9 (CH$_2$), 35.4 (CH), 0.9 (CH$_3$);

MS: m/z (%)=338 (84) [MH-CH$_4$$^+$], 354 (100) [MH$^+$], 729 (33) [2MNa$^+$].

MSHR m/z [MH$^+$] calculated for C$_{20}$H$_{23}$NO$_3$Si: 354.1525; found: 354.1519.

Elemental analysis: found (calculated) C, 68.16 (67.96); H, 6.58 (6.56); N, 3.92 (3.96);

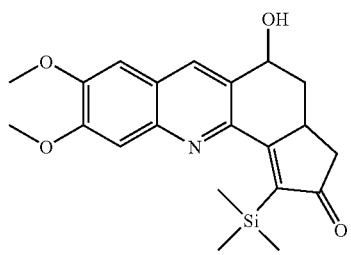 [SMILES: COc1cc2cc3c(nc2cc1OC)C1=C([Si](C)(C)C)C(=O)CC1CC3O]

5-Hydroxy-8,9-dimethoxy-1-trimethylsilanyl-3,3a,4,5-tetrahydro-2H-cyclopenta[c]acridin-2-one Mp 221-222° C.

IR: 3388, 2962, 2936, 2891, 2825, 1691, 1497, 1240, 846, 830 cm$^{-2}$.

$^1$H NMR (300 MHz, CDCl$_3$): δ=7.99 (s, 1H), 7.28 (s, 1H), 6.98 (s, 1H), 5.11-5.07 (m, 1H), 4.03 (s, 3H), 3.97 (s, 3H), 3.64-3.59 (m, 1H), 2.77 (dd, 1H, J=17.9, 6.8 Hz), 2.58-2.44 (m,1H), 2.21 (dd, 1H, J=17.9, 4.1 Hz), 1.88 (ddd, 1H, J=13.5, 13.5, 3.2 Hz), 1.24 (m, 1H), 0.35 (s, 9H);

$^{13}$C NMR (75 MHz, CDCl$_3$): δ=212.2 (C), 180.4 (C), 153.5 (C), 151.2 (C), 147.5 (C), 144.8 (C), 140.8 (C), 135.3 (CH), 131.3 (C), 124.6 (C), 107.2 (CH$_3$), 104.9 (CH$_3$), 67.7 (CH), 56.3 (CH), 56.2 (CH), 43.7 (CH$_2$), 38.1 (CH$_2$), 35.4 (CH), 1.0 (CH$_3$);

MS: m/z (%)=368 (79) [MH-CH$_4$$^+$], 384 (100) [MH$^+$], 789 (29) [2MNa$^+$].

MSHR m/z [MH$^+$] calculated for C$_{21}$H$_{25}$NO$_3$Si: 384.1631; found: 384.1636.

Elemental analysis: found (calculated +0.5H$_2$O) C, 63.82 (64.26); H, 6.36 (6.68); N, 3.57 (3.57);

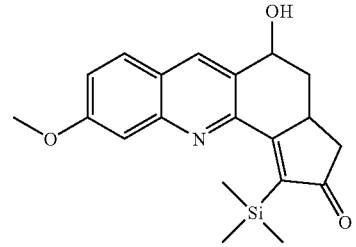 [SMILES: COc1ccc2cc3c(nc2c1)C1=C([Si](C)(C)C)C(=O)CC1CC3O]

5-Hydroxy-9-methoxy-1-trimethylsilanyl-3,3a,4,5-tetrahydro-2H-cyclopenta[c]acridin-2-one Mp 187° C.

IR: 3440, 2962, 2947, 2903, 2851, 1693, 1621, 1228, 1140, 1019, 848, 835, 819 cm$^{-1}$.

$^1$H NMR (300 MHz, CDCl$_3$): δ=8.09 (s, 1H), 7.66 (d, 1H, J=9.0 Hz), 7.31 (d, 1H, J=2.2 Hz), 7.19 (dd, 1H, J=9.0, 2.2 Hz), 5.10-5.08 (m, 1H), 3.95 (s, 3H), 3.66-3.56 (m, 1H), 2.75 (dd, 1H, J=18.0, 6.7 Hz), 2.48-2.42 (m, 1H), 2.17 (dd, 1H, J=18.0, 4.0 Hz), 1.85 (ddd, 1H, J=13.5, 13.5, 3.3 Hz), 0.35 (s, 9H);

$^{13}$C NMR (75 MHz, CDCl$_3$): δ=212.3 (C), 180.3 (C), 161.4 (C), 149.9 (C), 149.3 (C), 142.0 (C), 137.1 (CH), 130.8 (C), 128.8 (CH), 123.8 (C), 121.3 (CH), 106.8 (CH$_3$), 67.5 (CH), 55.6 (CH), 43.7 (CH$_2$), 38.1 (CH$_2$), 35.4 (CH), 0.9 (CH$_3$);

MS: m/z (%)=338 (66) [MH-CH$_4$$^+$], 354 (100) [MH$^+$], 729 (17) [2MNa$^+$].

MSHR m/z [MH$^+$] calculated for C$_{20}$H$_{23}$NO$_3$Si: 354.1525; found: 354.1531.

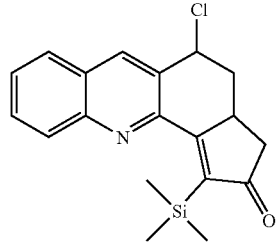 [SMILES: C[Si](C)(C)C1=C2c3nc4ccccc4cc3C(Cl)CC2CC1=O]

5-Chloro-1-trimethylsilanyl-3,3a,4,5-tetrahydro-2H-cyclopenta[c]acridin-2-one

The 5-hydroxy-1-trimethylsilanyl-3,3a,4,5-tetrahydro-2H-cyclopenta[c]acridin-2-one (323 mg, 1.00 mmol) is dissolved in 10 ml of freshly distilled DCM under an argon atmosphere at 0° C. SOCl$_2$ (182 µl, 2.5 mmol) is then added dropwise to the reaction medium, which is stirred at 0° C. for 15 min. The reaction medium is then run into a saturated aqueous solution of NaHCO$_3$, the aqueous phase is extracted with DCM and the resulting organic phase is rinsed with a saturated aqueous solution of NaCl, dried over Na$_2$SO$_4$, filtered and evaporated. The residue obtained is purified by flash chromatography.

Mp 169-170° C.

IR: 3038, 2952, 2897, 1687, 1491, 1219, 1195, 1157, 841, 770 cm$^{-1}$.

$^1$H NMR (300 MHz, CDCl$_3$): δ=8.24 (s, 1H), 8.11 (dd, 1H, J=8.4, 1.1 Hz), 7.85 (dd, 1H, J=8.1, 1.4 Hz), 7.78 (ddd, 1H, J=8.4, 7.0, 1.4 Hz), 7.61 (ddd, 1H, J=8.1, 7.0, 1.1 Hz), 5.64 (dd, 1H, J=3.5, 2.2 Hz), 3.87-3.77 (m, 1H), 2.90 (dd, 1H, J=17.9, 6.9 Hz), 2.71 (ddd, 1H, J=14.2, 3.9, 2.2 Hz), 2.34-2.24 (m, 2H), 0.37 (s, 9H);

$^{13}$C NMR (75 MHz, CDCl$_3$): δ=211.2 (C), 178.1 (C), 148.9 (C), 147.7 (C), 143.4 (C), 138.0 (CH), 131.3 (C), 131.0 (CH), 129.5 (CH), 128.3 (C), 128.2 (CH), 128.0 (CH), 57.1 (CH), 43.3 (CH$_2$), 38.7 (CH$_2$), 35.8 (CH), 0.9 (CH$_3$);

MS: m/z (%)=326 (92) [MH-CH$_4^+$], 342 (100) [MH$^+$].

MSHR m/z [MH$^+$] calculated for C$_{19}$H$_{20}$ClNOSi: 342.1081; found: 342.1079.

Obtaining the enantiomers of 5-hydroxy-1-trimethylsilanyl-3,3a,4,5-tetrahydro-2H-cyclopenta[c]acridin-2-one The enantiomer forms are obtained according to scheme 1 below:

Variant Synthesis of Derivatives According to the Invention

This variant is illustrated by scheme 2 below, relating to the synthesis of 5-hydroxy-7-amino-8-methoxy-1-trimethylsilyl-3,3a,4,5-tetrahydro-2H-cyclopenta[c]acridin-2-one:

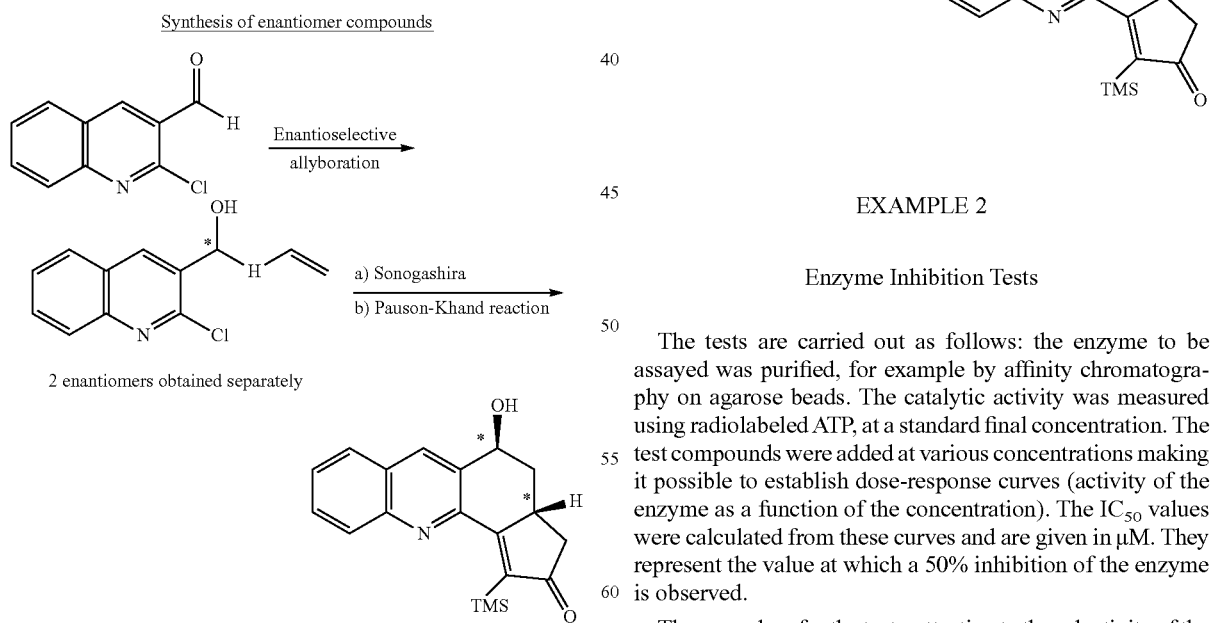

EXAMPLE 2

Enzyme Inhibition Tests

The tests are carried out as follows: the enzyme to be assayed was purified, for example by affinity chromatography on agarose beads. The catalytic activity was measured using radiolabeled ATP, at a standard final concentration. The test compounds were added at various concentrations making it possible to establish dose-response curves (activity of the enzyme as a function of the concentration). The IC$_{50}$ values were calculated from these curves and are given in µM. They represent the value at which a 50% inhibition of the enzyme is observed.

The procedure for the tests, attesting to the selectivity of the compounds of type (I) for the target kinases (versus 70 other kinases), was recently reported (4).

The value of the IC$_{50}$s measured with compounds of the invention, with respect to CDK1 and CDK5, are reported in the following table 1:

TABLE 1

| Compound | CDK1 | CDK5 |
| --- | --- | --- |
| 5-hydroxy-1-trimethylsilanyl-3,3a,4,5-tetrahydro-2H-cyclopenta[c]acridin-2-one (racemic) | 0.56 to 0.74 | 1.6 to 2.3 |
| 5-hydroxy-1-trimethylsilanyl-3,3a,4,5-tetrahydro-2H-cyclopenta[c]acridin-2-one (+ enantiomer) | 0.62 | 3 |
| 5-hydroxy-1-trimethylsilanyl-3,3a,4,5-tetrahydro-2H-cyclopenta[c]acridin-2-one (− enantiomer) | 7.8 | 26 |
| 5-chloro-1-trimethylsilanyl-3,3a,4,5-tetrahydro-2H-cyclopenta[c]acridin-2-one | 3.6 | 63 |
| 5-hydroxy-8-methoxy-1-trimethylsilanyl-3,3a,4,5-tetrahydro-2H-cyclopenta[c]acridin-2-one | 1.7 | 4 |
| 5-hydroxy-8,9-methoxy-1-trimethylsilanyl-3,3a,4,5-tetrahydro-2H-cyclopenta[c]acridin-2-one | 1.7 | 3.3 |
| 5-hydroxy-9-methoxy-1-trimethylsilanyl-3,3a,4,5-tetrahydro-2H-cyclopenta[c]acridin-2-one | 1.6 | 4.8 |

The 5-hydroxy-1-trimethylsilanyl-3,3a,4,5-tetrahydro 2H-cyclopenta[c]acridin-2-one has an $IC_{50}$ with $IC_{50}$ values of 0.54 µM with respect to CDK1 and of 1.6 µM with respect to CDK5.

EXAMPLE 3

Cytotoxic Activity Tests

The tests are carried out on HT29 cells (human colon adenocarcinoma, deposit ATCC HTB 38) with the procedure as follows:

The HT29 cells are cultured in Dulbecco's MEM medium supplemented with 10% FCS. The cells originating from a log-phase culture are seeded into 24-well microplates (1 ml-5×10⁴ cells/well) and incubated for 2 days. The compounds tested, in solution in DMSO (dimethyl sulfoxide), are added in a minimum volume (5 µl) at increasing concentration. The control cells receive only 5 µl of DMSO alone. The plates are incubated for 24 h, then the medium is removed and the cells are washed twice with PBS (phosphate buffered saline solution) before medicament-free fresh medium is added. The plates are re-incubated for 3 days before evaluation of the cell survival using the MTT test (5) which comprises Incubating 3-[4,5-dimethylthiazol-2-yl]-2,5-diphenyl tetrazolium bromide (MTT, Sigma) for 30 min in wells, in a proportion of 100 µg/well. After removal of the medium, the formazan crystals are recovered with 100 µl of DMSO and the absorbance is measured at 540 nm with a microplate reader (model 450, Bio-Rad). The cell survival is expressed as % of the controls treated with DMSO.

The results are given in the following Table 2:

TABLE 2

| Compound tested | $IC_{50}$ (HT 29-24 h) |
| --- | --- |
| 5-Hydroxy-1-trimethylsilanyl-3,3a,4,5-tetrahydro-2H-cyclopenta[c]acridin-2-one | 26 |
| 5-Hydroxy-8-methoxy-1-trimethylsilanyl-3,3a,4,5-tetrahydro-2H-cyclopenta[c]acridin-2-one | 21 |

TABLE 2-continued

| Compound tested | $IC_{50}$ (HT 29-24 h) |
| --- | --- |
| 5-Hydroxy-8,9-dimethoxy-1-trimethylsilanyl-3,3a,4,5-tetrahydro-2H-cyclopenta[c]acridin-2-one | 41 |
| 5-Hydroxy-9-methoxy-1-trimethylsilanyl-3,3a,4,5-tetrahydro-2H-cyclopenta[c]acridin-2-one | 6.5 |

EXAMPLE 4

MTS Tests

The viability of SHSY cells is determined by measuring the MTS reduction as described in (6).

The results obtained are given in the following Table 3:

TABLE 3

| Compound | % survival of SHSY cells at 10 µM | $IC_{50}$ at 48 h |
| --- | --- | --- |
| 1-(2-(Trimethylsilanylethynyl)quinolin-3-yl)propan-2-en-1-ol | 0.4 | 6.1 |
| 1-(2-[3-(Tetrahydropyran-2-yloxy)prop-1-ynyl]quinolin-3-yl)but-3-en-1-ol | 2 | 5.1 |
| 1-(2-(Diethoxyethynyl)quinolin-3-yl)but-3-en-1-ol | 2 | 5.2 |
| 1-(2-Trimethylsilanylethynyl)quinolin-3-yl)propan-3-nitro-1-one | 47 | 15 |
| 5-Keto-1-butyl-3,3a,4,5-tetrahydro-2H-cyclopenta[c]acridin-2-one | 38 | 13 |
| 1-(2-(Pyridin-2-ylethynyl)quinolin-3-yl)ethanone | 4 | 10 |
| 5-Hydroxy-9-methoxy-1-trimethylsilanyl-3,3a,4,5-tetrahydro-2H-cyclopenta[c]acridin-2-one | 44 | 13 |
| 5-Hydroxy-1-trimethylsilanyl-3,3a,4,5-tetrahydro-2H-cyclopenta[c]acridin-2-one (racemic) | 85 | >10 |

REFERENCES

1. Patin A. and Belmont P., Synthesis, 2005, 2400-2406
2. Meth-Cohn O., Narine B., Tarnowski B., J. Chem. Soc, Perkin Trans. 1, 1981, 1520 and 1531.
3. Kolb H. C, Finn M. G. and Sharpless K. B., 2001, Angew. Chem. Int. Ed. 40, 2004-2021.
4. Bain J., Plater L., Elliott M., Shpiro N., Hastie C. J., Mclauchlan H., Klevernic I., Arthur J. S. C, Alessi D. R. and Cohen P., Biochem. J., 2007, 408, 297-315.
5. Mossmann T., J. Immunol. Meth., 1983, 65, 55-63.
6. Ribas J. and Boix J., 2004, Exp. Cell Res., 295, 9-24.

The invention claimed is:

1. A kinase inhibitor compound of formula (I)

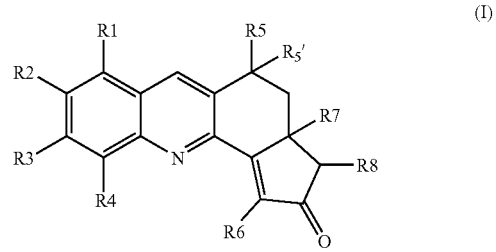

(I)

in which:

$R_1$ to $R_4$, which may be identical or different, represent H; an ether radical —OR, wherein R represents a linear or branched $C_1$-$C_{12}$ alkyl radical; an amino group $NH_2$ or $N(R_9, R_{10})$; $NO_2$; NH-carbamate of —NH—CO-OM type, with M representing R or a salt; NH—CO—R; $N_3$ or derivatives thereof with a 1,2,3-triazole cycle;

$R_5$ represents an —OH group; halogen; —OR with R as defined above with respect to $R_1$-$R_4$; OH-carbamate of —O—CO—NHM type, with M representing R, as defined above with respect to $R_1$-$R_4$; OH-carbonate of —O—CO—OM type, with M representing R, as defined above with respect to $R_1$-$R_4$; $NH_2$, NH-carbamate of —NH—CO-OM type, with M representing R, or a salt; NH—CO—R with R as defined above with respect to $R_1$-$R_4$; $N_3$ or derivatives thereof with a 1,2,3-triazole cycle; or $N(R_9, R_{10})$;

$R_5'$ represents H or a $C_1$-$C_{12}$ alkyl radical, or $R_5/R_5'$ together represents an =O group;

$R_6$ represents H; the R radical; an (R or R')$_3$—Si group, R being as defined above with respect to $R_1$-$R_4$; an aryl radical, where appropriate substituted, a heteroaryl radical; a halogen; or an alkynyl radical —C≡C—R;

$R_7$ and $R_8$, which may be identical or different, represent an H or a $C_1$-$C_{12}$ alkyl radical;

$R_9$ and $R_{10}$, which may be identical or different, represent H or the R-radical, with the exception of the compounds in which $R_1$-$R_4$, $R_7$ and $R_8$=H, $R_5$ and $R_5'$ form a —C=O group, and $R_6$=—$(CH_3)_3$—Si, —$C_6H_5$, or $C_1$ or $C_4$ alkyl; $R_1$-$R_4$, $R_7$ and $R_8$=H, $R_5$=OH and $R_5'$=H, and $R_6$=—$(CH_3)_3$—Si, —$C_6H_5$, or $C_1$ or $C_4$ alkyl; $R_1$-$R_4$, $R_7$ and $R_8$=H, $R_5$=H and $R_5'$=OH, and $R_6$=—$(CH_3)_3$—Si, —$C_6H_5$, or $C_1$ or $C_4$ alkyl; $R_1$-$R_4$, $R_7$ and $R_8$=H, $R_5$=—$OCH_3$ and $R_5'$=H, and $R_6$=$C_4$ alkyl; and $R_1$-$R_4$, $R_7$ and $R_8$=H, $R_5$=H and $R_5'$=—$OCH_3$, and $R_6$=$C_4$ alkyl.

2. A compound of claim 1, that is a CDK-selective inhibitor.

3. The CDK-selective inhibitor as claimed in claim 2, that exhibits, with respect to CDK1 and to CDK5, an $IC_{50}$ value of less than 20 μM.

4. Compounds of the general formula (I) in a racemic or enantiomeric form

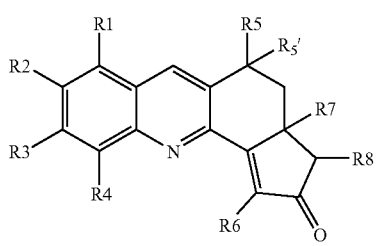

(I)

in which:

$R_1$ to $R_4$, which may be identical or different, represent H; an ether radical —OR, wherein R represents a linear or branched $C_1$-$C_{12}$ alkyl radical; an amino group $NH_2$ or $N(R_9, R_{10})$; $NO_2$; NH-carbamate of —NH—CO-OM type, with M representing R or a salt; NH—CO—R; $N_3$ or derivatives thereof with a 1,2,3-triazole cycle;

$R_5$ represents an —OH group; halogen; —OR with R as defined above with respect to $R_1$-$R_4$; OH-carbamate of —O—CO—NHM type, with M representing R, as defined above with respect to $R_1$-$R_4$; OH-carbonate of —O—CO-OM type, with M representing R, as defined above with respect to $R_1$-$R_4$; $NH_2$, NH-carbamate of —NH—CO-OM type, with M representing R, or a salt; NH—CO—R with R as defined above with respect to $R_1$-$R_4$; $N_3$ or derivatives thereof with a 1,2,3-triazole cycle; or $N(R_9, R_{10})$;

$R_5'$ represents H or a $C_1$-$C_{12}$ alkyl radical, or $R_5/R_5'$ together represents an =O group;

$R_6$ represents H; the R radical; an (R or R')$_3$—Si group, R being as defined above with respect to $R_1$-$R_4$; an aryl radical, where appropriate substituted, a heteroaryl radical; a halogen; or an alkynyl radical —C≡C—R;

$R_7$ and $R_8$, which may be identical or different, represent an H or a $C_1$-$C_{12}$ alkyl radical;

$R_9$ and $R_{10}$, which may be identical or different, represent H or the R radical, with the exception of the compounds in which $R_1$-$R_4$, $R_7$ and $R_8$=H, $R_5$ and $R_5'$ form a —C=O group, and $R_6$=—$(CH_3)_3$—Si, —$C_6H_5$, or $C_1$ or $C_4$ alkyl; $R_1$-$R_4$, $R_7$ and $R_8$=H, $R_5$=OH and $R_5'$=H, and $R_6$=—$(CH_3)_3$—Si, —$C_6H_5$, or $C_1$ or $C_4$ alkyl; $R_1$-$R_4$, $R_7$ and $R_8$=H, $R_5$=H and $R_5'$=OH, and $R_6$=—$(CH_3)_3$—Si, —$C_6H_5$, or $C_1$ or $C_4$ alkyl; $R_1$-$R_4$, $R_7$ and $R_8$=H, $R_5$=—$OCH_3$ and $R_5'$=H, and $R_6$=$C_4$ alkyl; and $R_1$-$R_4$, $R_7$ and $R_8$=H, $R_5$=H and $R_5'$=—$OCH_3$, and $R_6$=$C_4$ alkyl.

5. A compound selected from the group consisting of 5-hydroxy-1-trimethylsilanyl-3,3a,4,5-tetrahydro-2H-cyclopenta[c]acridin-2-one, 5-hydroxy-8-methoxy-1-trimethylsilanyl-3,3a,4,5-tetrahydro-2H-cyclopenta[c]acridin-2-one, 5-hydroxy-8,9-dimethoxy-1-trimethylsilanyl-3,3a,4,5-tetrahydro-2H-cyclopenta[c]acridin-2-one, 5-hydroxy-9-methoxy-1-trimethylsilanyl-3,3a,4,5-tetrahydro-2H-cyclopenta[c]acridin-2-one, 5-hydroxy-1-tert-butyl-3,3a,4,5-tetrahydro-2H-cyclopenta[c]acridin-2-one, 5-hydroxy-8-methoxy-1-tert-butyl-3,3a,4,5-tetrahydro-2H-cyclopenta[c]acridin-2-one, 5-hydroxy-1-trimethylsilanyl-3-methyl-3,3a,4,5-tetrahydro-2H-cyclopenta[c]acridin-2-one, 5-hydroxy-9-methoxy-1-trimethylsilanyl-3-methyl-3,3a,4,5-tetrahydro-2H-cyclopenta[c]acridin-2-one, 5-chloro-1-trimethylsilanyl-3,3a,4,5-tetrahydro-2H-cyclopenta[c]acridin-2-one, 5-keto-3,3a,4,5-tetrahydro-2H-cyclopenta[c]acridin-2-one, 5-hydroxy-1-butanyl-3,3a,4,5-tetrahydro-2H-cyclopenta[c]acridin-2-one, 5-keto-1-trimethylsilanyl-3,3a,4,5-tetrahydro-2H-cyclopenta[c]acridin-2-one, and 5-hydroxy-3,3a,4,5-tetrahydro-2H-cyclopenta[c]acridin-2-one.

6. A compound selected from the group consisting of 5-hydroxy-8-methoxy-1-trimethylsilanyl-3,3a,4,5-tetrahydro-2H-cyclopenta[c]acridin-2-one, 5-hydroxy-8,9-dimethoxy-1-trimethylsilanyl-3,3a,4,5-tetrahydro-2H-cyclopenta[c]acridin-2-one, 5-hydroxy-9-methoxy-1-trimethylsilanyl-3,3a,4,5-tetrahydro-2H-cyclopenta[c]acridin-2-one, 5-hydroxy-1-tert-butyl-3,3a,4,5-tetrahydro-2H-cyclopenta[c]acridin-2-one, 5-hydroxy-8-methoxy-1-tert-butyl-3,3a,4,5-tetrahydro-2H-cyclopenta[c]acridin-2-one, 5-hydroxy-1-trimethylsilanyl-3-methyl-3,3a,4,5-tetrahydro-2H-cyclopenta[c]acridin-2-one, 5-hydroxy-9-methoxy-1-trimethylsilanyl-3-methyl-3,3a,4,5-tetrahydro-2H-cyclopenta[c]acridin-2-one, 5-chloro-1-trimethylsilanyl-3,3a,4,5-tetrahydro-2H-cyclopenta[c]acridin-2-one, and 5-hydroxy-3,3a,4,5-tetrahydro-2H-cyclopenta[c]acridin-2-one.

7. A pharmaceutical composition comprising a therapeutically effective amount of at least one compound formula (I)

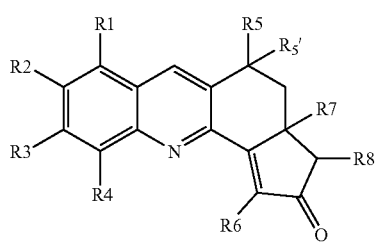

(I)

in which:

$R_1$ to $R_4$, which may be identical or different, represent H; an ether radical —OR, wherein R represents a linear or branched $C_1$-$C_{12}$ alkyl radical; an amino group $NH_2$ or $N(R_9, R_{10})$; $NO_2$; NH-carbamate of —NH—CO-OM type, with M representing R or a salt; NH—CO—R; $N_3$ or derivatives thereof with a 1,2,3-triazole cycle;

$R_5$ represents an —OH group; halogen; —OR with R as defined above with respect to $R_1$-$R_4$; OH-carbamate of —O—CO—NHM type, with M representing R as defined above with respect to $R_1$-$R_4$; OH-carbonate of —O—CO-OM type, with M representing R as defined above with respect to $R_1$-$R_4$; $NH_2$, NH-carbamate of —NH—CO-OM type, with M representing R or a salt; NH—CO—R with R as defined above with respect to $R_1$-$R_4$; $N_3$ or derivatives thereof with a 1,2,3-triazole cycle; or $N(R_9, R_{10})$, M and R being as defined above with respect to $R_5$;

$R_5'$ represents H or a $C_1$-$C_{12}$ alkyl radical, or $R_5/R_5'$ together represents an =O group;

$R_6$ represents H; the R radical; an (R or R')$_3$—Si group; an aryl radical, where appropriate substituted, a heteroaryl radical; a halogen; or an alkynyl radical —C≡C—R, with R as defined above with respect to $R_1$-$R_4$;

$R_7$ and $R_8$, which may be identical or different, represent an H or a $C_1$-$C_{12}$ alkyl radical;

$R_9$ and $R_{10}$, which may be identical or different, represent H or the R radical, and a pharmaceutically acceptable carrier; said composition being in an orally administrable, parenterally administrable or injectable form.

8. The composition as claimed in claim 7, in the form of tablets, gel capsules, capsules, pills, sugar-coated tablets, or drops.

9. The composition as claimed in claim 7, in an intravenously administrable form, subcutaneously injectible form or intramuscularly injectible form.

10. A pharmaceutical composition comprising a compound of claim 5 and a pharmaceutically acceptable carrier.

11. A pharmaceutical composition comprising a compound of claim 6 and a pharmaceutically acceptable carrier.

12. A method of treating diabetes, depression or bipolar disorder comprising administering a compound of claim 1 to a person in need to said treatment.

13. A method of treating diabetes, depression or bipolar disorder comprising administering a composition of claim 8 to a person in need to said treatment.

14. A method of treating diabetes, depression or bipolar disorder comprising administering a compound of claim 5 to a person in need to said treatment.

15. A method of treating diabetes, depression or bipolar disorder comprising administering a composition of claim 10 to a person in need to said treatment.

\* \* \* \* \*